United States Patent [19]

Christiansen

[11] Patent Number: 5,738,633
[45] Date of Patent: Apr. 14, 1998

[54] OTO-ACOUSTIC EMISSION ANALYSER

[75] Inventor: Christian Christiansen, Herley, Denmark

[73] Assignee: Madsen Electronics A/S, Taastrup, Denmark

[21] Appl. No.: 646,336

[22] PCT Filed: Dec. 6, 1994

[86] PCT No.: PCT/DK94/00458

§ 371 Date: Jun. 6, 1996

§ 102(e) Date: Jun. 6, 1996

[87] PCT Pub. No.: WO95/15712

PCT Pub. Date: Jun. 15, 1995

[30] Foreign Application Priority Data

Dec. 10, 1993 [DK] Denmark ................ 1387/93

[51] Int. Cl.⁶ .................................................. A61B 5/00
[52] U.S. Cl. .................................................... 600/559
[58] Field of Search ................... 128/746; 73/585, 73/587; 381/54; 600/559

[56] References Cited

U.S. PATENT DOCUMENTS

| | | | |
|---|---|---|---|
| 3,698,387 | 10/1972 | Moore et al. | 128/9 |
| 4,057,051 | 11/1977 | Kerouac | 128/2 |
| 4,374,526 | 2/1983 | Kemp | 128/746 |
| 4,567,881 | 2/1986 | Heller | 128/9 |
| 4,601,295 | 7/1986 | Teele | 128/746 |
| 4,688,582 | 8/1987 | Heller et al. | 128/746 |
| 5,239,984 | 8/1993 | Cane et al. | 128/9 |
| 5,526,819 | 6/1996 | Lousbury-Martin et al. | 128/746 |
| 5,546,956 | 8/1996 | Thornton | 128/746 |
| 5,577,511 | 11/1996 | Killion | 128/746 |
| 5,594,174 | 1/1997 | Keefe | 128/746 X |

FOREIGN PATENT DOCUMENTS

| | | |
|---|---|---|
| WO 93/20746 | 10/1993 | WIPO . |
| WO 94/22372 | 10/1994 | WIPO . |

*Primary Examiner*—Francis Jaworski
*Attorney, Agent, or Firm*—Merchant, Gould, Smith, Edell, Welter, & Schmidt, P.A.

[57] ABSTRACT

A hand-held, battery-driven, oto-acoustic emission analyzer comprises an apparatus housing with two areas; an elongated housing part for electronic circuits, a measuring probe and a display, and a handgrip part for containing a power supply unit in the form of a battery compartment and a pump, such as a mechanical, hand-operated pump.

10 Claims, 3 Drawing Sheets

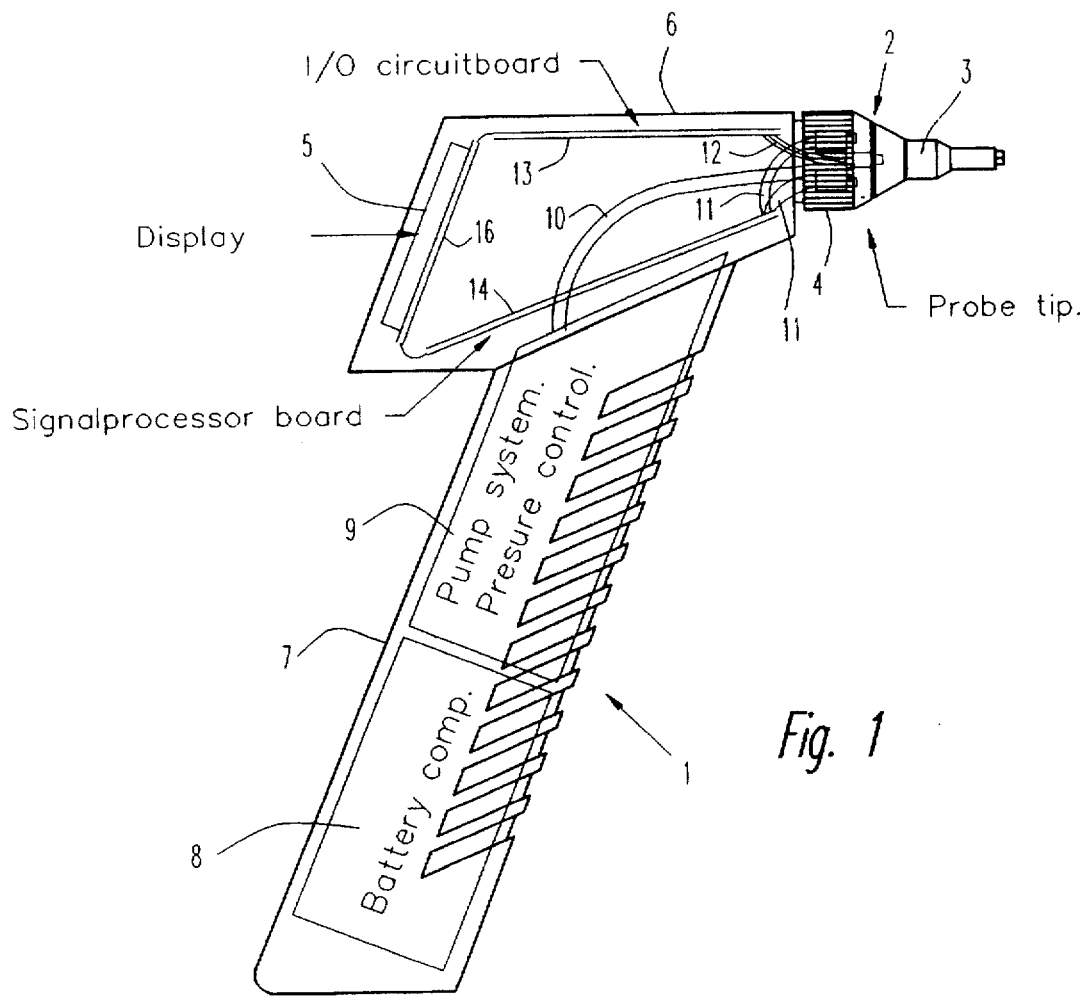
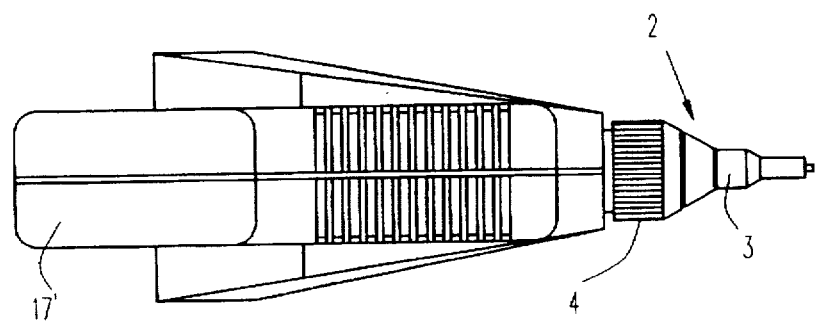

OTO-ACOUSTIC EMISSION ANALYSER

BACKGROUND OF THE INVENTION

The invention relates to an oto-acoustic emission analyser.

Such an apparatus is used for audiometric emission measurements on an individual, e.g. a person whose hearing ability is to be examined. Emission-like measurements are discussed for the first time in Danish patent no. 147,726 (U.S. Pat. No. 4,374,526), in which the British researcher D. T. Kemp deals with the measurement of echo signals from a person's inner ear, i.e. measuring of an acoustic echo brought about by introducing an acoustic signal in the form of a transient audio signal into the ear by means of a transducer. This measuring technique has since been further developed, and it has now become apparent that what is involved is not an echo but a stimulated emission from the inner ear. It has subsequently been ascertained that the emission can be stimulated in other ways, e.g. by using tone pairs, so-called stimulus signals, which consist of two or more pairs of substantially sinusoidal oscillations, these pairs having frequencies which lie relatively close to each another, e.g. so that one signal has a frequency in the range of 1.2 times the other frequency. This technique is described, for example, in international application no. WO 93/20746. Others have developed other signal combinations which can also stimulate the inner ear to provide measurable emission signals.

As a minimum, an emission measurement thus requires a measuring probe to be introduced into the ear of the person on whom the measurement is to be carried out, said probe comprising at least one, or preferably two, transducers for the generation of stimulus signals, and at least one transducer for measurement of the emission signal, plus an associated electronic circuit, partly for the generation of the signals and partly for the processing of the emission signals. Equipment of this kind has hitherto been produced as table-type apparatus of a certain size, to which a long cable is connected. One end of the cable is connected to the table apparatus, and the other end of the cable is connected to a probe unit with a measuring probe. For example, such an apparatus is depicted and explained in Danish patent application no. 393/93, which is owned by the applicant of the present application. Such table-type equipment can carry out the desired measurements, but it is required that the person or the individual to be measured is brought to the equipment, which can often be inexpedient. It is particularly inexpedient if systematic measurements, so-called screening, are to be carried out on a certain group of the population, e.g. newborn babies. Table-type equipment with cable and measuring probe also often suffers the disadvantage that a calibration is required if the probe is replaced.

Other types of audiometric apparatus are known for the screening of a population group, where the apparatus is portable, e.g. carried in the hand. A hand-held tympanometer, i.e. an apparatus for measuring the acoustic impedance in the outer ear under varying pressure conditions, is known from U.S. Pat. No. 4,688,582. However, such an apparatus provides only limited information concerning the person's possible hearing ailment. Consequently, there is a need for an apparatus which can carry out more detailed measurements and thereby provide a considerably better sceening result.

SUMMARY OF THE INVENTION

The apparatus according to the invention, has the advantage that it is completely portable, so that it is possible, e.g. at a hospital, in a school or similar institution, to quickly carry out a screening for hearing ailments by an oto-acoustic emission measurement on each individual. The apparatus according to the invention, since it does not take up much room or weigh very much, can also form part of the equipment carried by health care personnel or by practising doctors, so that these people while on their rounds or sick calls or other visits to the home, e.g. in connection with a birth or the like, can more easily undertake a routine examination or possibly make a diagnosis. Especially in the examination of children or other people with whom it is difficult or impossible to communicate, the apparatus according to the invention is a very great help in making diagnoses of impairments of those organs which form part of the hearing.

The apparatus according to the invention may be configured with a replaceable tip for reasons of hygiene, without it being necessary to calibrate the apparatus after the replacement.

By configuring the apparatus with a pump connected via an air hose to the measuring probe, the pump can be used to carry out a so-called middle-ear compensation. If the eardrum is distended in an arc, i.e. due to an overpressure or an underpressure in the middle ear, this can be compensated for by applying a corresponding pressure or underpressure in the area of the ear canal which is blocked by means of the probe tip. Compensation is hereby made for the changed flexibility of the eardrum due to the pressure or the overpressure, while the result that the emission measurement can still be used. Placing of the pump in the handgrip gives the apparatus good balance with regard to weight.

The pump can be electrically-driven or hand-operated. Where the pump is hand-operated, the cost of the apparatus and its power consumption and weight can be reduced, which is extremely desirable. For example, the pump can consist of a rubber ball or bellows or the like, and with corresponding over- and underpressure valves.

The apparatus according to the invention may be configured with a battery and power supply in a handgrip, so that the resulting apparatus lies good and stable in the hand. The handgrip is particularly suitable for housing the pump and the battery, so that from the weight point of view the apparatus is well-balanced and herewith easy to use without causing any unnecessary discomfort to the person being examined. The battery can either be of the re-chargeable type, or ordinary, replaceable batteries can be used.

The apparatus according to the invention can be configured so that the tip of the probe comprises a seal against the ear canal, said seal being made of soft, deformable material so that a good seal is achieved without causing the person being examined any unnecessary discomfort.

In another embodiment, the apparatus according to the invention is configured with the probe at one end of an elongated part and the display at the other end. The apparatus thus achieved is easy and logical in use, is well-balanced and is simple and quick to adjust and to use.

The apparatus according to the invention can also be configured for communication of information with other apparatus. For example, the apparatus can be arranged in a manner which allows the data collected in the apparatus to be transferred to other apparatus, and possibly such that the apparatus can be simultaneously supplied with current for the charging of the battery. The transfer of data can be carried out via a plug connection, but can also be effected by transmission, e.g. by means of radio waves, sound waves or in another commonly-known manner.

BRIEF DESCRIPTION OF THE FIGURES

An example embodiment according to the invention is shown in the drawing and is described in more detail in the following, in that FIG. 1 shows the apparatus as a whole seen from the side, substantially in full size, and where parts of the apparatus are shown transparent, FIG. 4 shows the apparatus in FIG. 1 seen from underneath.

DESCRIPTION OF THE EXAMPLE EMBODIMENT

Figure 2:
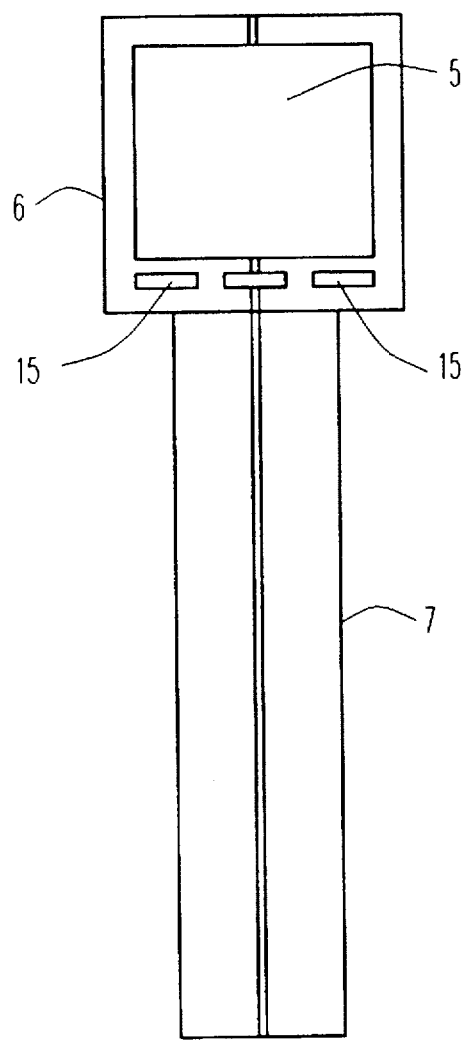
FIG. 2 shows the apparatus in FIG. 1 seen towards that side in which the display is disposed.
Figure 3:
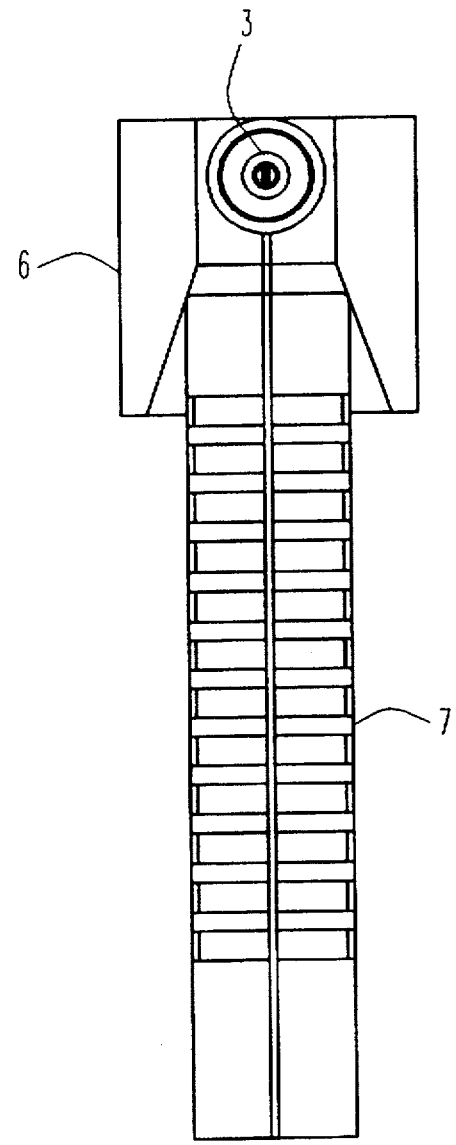
FIG. 3 shows the apparatus in FIG. 1 seen from the front in towards the measuring probe.

FIGS. 1–4 of the drawing show an oto-acoustic emission analyser 1 according to the invention built completely into an apparatus housing consisting of two housing parts, i.e. the handgrip part 7 and an elongated housing part 6 integral herewith. The housing part 6 is pointed or arrow-shaped towards that end at which the measuring probe 2 is mounted, see FIGS. 1–4. The measuring probe 2 comprises a probe housing 4 which is surrounded by a union which secures the replaceable probe tip 3, e.g. configured as shown and explained in the applicant's earlier Danish patent application no. 393/93. The housing part 6 also comprises a display 5, e.g. an LCD display, and a keypad or a number of operating keys 15 disposed on that side which faces towards the person who operates the apparatus. The display 5 is mounted on a printed circuit 16 which constitutes a display control circuit inside the housing part 6, which in addition houses two or more prints 13, 14 respectively with the input/output circuits 13 for the transducers, and which are explained later with reference to FIG. 5, plus a data-processing print 14 which is similarly explained later with reference to FIG. 5. Signal leads 11, 12 extend from the two prints 13, 14 to the transducers 33, 34, 35 disposed inside the measuring probe 2 and as shown and explained in connection with FIG. 5. Moreover, the housing part 6 can also contain other electrical or electronic circuits and components which are explained later with reference to FIG. 5.

The handgrip part 7 comprises two areas, i.e. an area 9 for a pump with associated valves, e.g. a manual pump, and an area 8 arranged a battery compartment, e.g. for a rechargeable battery or an ordinary battery. One side of the handgrip 7 is configured with ribs or the like which provide a good grip, and possibly in such a manner that a pump in the handgrip can be influenced by a hand around the handgrip, said pump being, for example, a rubber ball or bellows or a tube that can be deformed when the handgrip is squeezed. The part area 9 for the pump also houses the necessary overpressure and underpressure valves which, via the tube 10, lead to the probe tip 3 from the pump, e.g. in a manner corresponding to that explained in the applicant's earlier Danish patent application no. 393/93. The valves ensure that a pressure which is too high or too low cannot inadvertently be applied and thus irritate or injure a person who is to be examined.

Plug connections or the like can be provided in the bottom surface 17' of the free end of the handgrip 7, so that the apparatus according to the invention can be connected to a charging unit for the charging of re-chargeable batteries.

There can also be means which enable the apparatus to be in data communication with other apparatus to which stored measurement information and the like is to be transferred. These means can simply be a plug connection, but other means can also be used, e.g. if the communication is effected by means of radio waves, sound waves or in another known manner.

The function of the apparatus will now be described with reference to FIG. 5 of the drawing, which shows a complete block diagram of the apparatus. For the sake of clarity, the same reference numbers are used for those parts or circuits in FIG. 5 which correspond to parts shown in FIGS. 14–.

Figure 5:
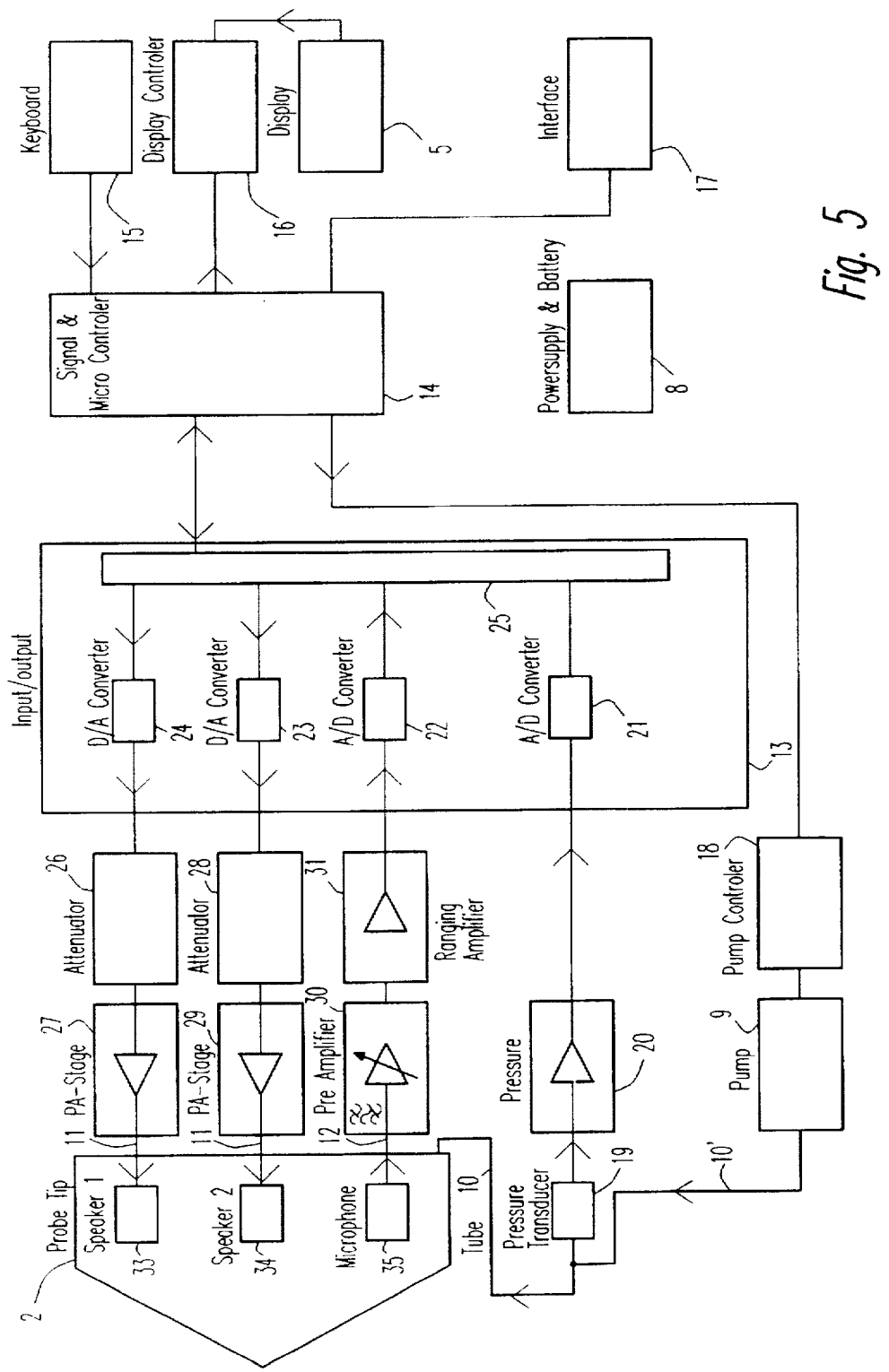
FIG. 5 shows a complete, electronic block diagram of the electrical and electronic circuits for the apparatus.

In the upper right-hand corner of FIG. 5 there is shown a block 15 which symbolizes a keypad or a number of operating keys. When the apparatus is switched on and set for measuring, an emission measurement is carried out by introducing the probe tip into the ear canal of the person to be examined, and activation of one of the keys 15. Possibly at the same time herewith, the pump 9 is used to effect a change in pressure in the blocked area of the ear canal between the eardrum and the probe 2. Via the keypad 15 there is selected a measuring sequence which is executed by the signal processor circuit 14, which comprises a digital microprocessor, in that signals from here are sent to the control circuit 25 for the input/output circuit 13.

From here, the transducers 33, 34 are activated via the digital/analogue converters 23, 24, in that the levels are regulated via the attenuators 26, 28 and the output amplifiers 27, 29, and the stimulus signal is applied to the person being examined via the transducers 33, 34. The stimulus signal can be a sequence of tone pairs, a transient signal or other signal combinations as discussed earlier. The acoustic emission from the inner ear is scanned with a measuring transducer (microphone) 35, from where the signal is fed via a pre-amplifier 30, which can comprise suitable filter circuits, further via a ranging amplifier 31 to an analogue/digital converter 22 to the control circuit 25 in the input/output circuit 13. The signal, which is now in digital form, is fed from here to the signal processing circuit 14 where all the filtering and data processing is effected, in that the signal processing circuit 14 carries out the storage, the processing and the presentation of the signal values on the display, which is controlled via a display control circuit 16.

Via an interface circuit 17, which comprises the communication means 17' which are shown sketched in FIG. 4, signals stored in the signal processing circuit 14 can be sent to other units, e.g. stationary units for further data processing, registration, printout etc. Moreover, data or other signals can be fed into the microprocessor circuit 14 via the interface circuit 17, e.g. concerning measuring frequencies or other programming or control data for the signal processing circuit 14.

A suitable overpressure or underpressure can be established with the pump 9. The amount of pressure is regulated by the control unit 18 which is controlled by the microprocessor circuit 14. The pressure is conducted to the measuring probe 2 via the tubes 10' and 10, and is fed forward to the blocked area between the probe and the eardrum, e.g. by the probe being arranged as explained in the applicant's earlier Danish patent application no. 393/93 or in another known manner. The actual pressure is scanned with a pressure-measuring transducer 19, from which the signal is fed via a signal amplifier 20 and an analogue/digital converter 21 to the control circuit 25 in the input/output circuit, and from here further to the microprocessor circuit 14.

The power supply unit 8, which comprises batteries and power supply circuits for the individual electrical or electronic units, is not shown in further detail, in that this is configured in a commonly-known manner.

By feeding suitable sets of data into the microprocessor circuit 14, the oto-acoustic emission analyser according to the invention can be changed to be able to carry out other known measurements in connection with examinations of the hearing ability, these measurements being based on the application of sound to a person's ear canal, and possible scanning of the sound signals in the same place, e.g. while at the same time varying or adjusting the pressure in the ear canal to a certain amount.

The parts 6,7, which together constitute the apparatus housing, can be made of plastic, e.g by injection moulding in a commonly-known manner, or the housing can be made of an alloy. The housing can be configured as several parts which can be removed singly for the repair, servicing, adjustment etc. of the apparatus. If replaceable batteries are used, the power supply unit 8 can comprise a battery cover.

The housing part 6, which narrows down towards the measuring probe 2, is capable in the shown embodiment of housing substantially all of the electronic circuits shown in FIG. 5, i.e. the printed circuit boards 13, 14 and 16, as also shown in FIG. 1, and in the area between these boards are placed the amplifiers 27, 29, 30, 31 and the attenuators 26, 28, e.g. in the form of one or more extra prints or flexprints.

In the shown embodiment, the handgrip part 7 forms an angle of approx. 100°–120° to the housing part 6 and the longitudinal axis of the measuring probe 2.

The measuring apparatus achieved with this configuration is balanced from the point of view of weight, and is thus easy to use without causing the person to be examined any significant degree of discomfort. During a sequence of measurement, the apparatus is held with one hand, and the pump can be operated in a simple and convenient manner with the same hand if this is necessary for the execution of the measurement.

I claim:

1. Apparatus for measuring oto-acoustic emission from a person's inner ear, comprising:

a measuring probe having at least one signal generator, and at least one signal receiver, the measuring probe adapted for introduction into the person's outer ear, an electronic circuit for generating stimulus signals, including acoustic signals, and for measuring and processing signals emitted by the person's inner ear in response to a stimulus signal from the at least one signal generator, a display to display values of the signals, a power supply unit to supply electrical power to the measuring probe, the electronic circuit and the display, and a housing to hold the measuring probe, the electronic circuit, the display and the power supply unit, the housing being adapted to be held in a user's hand.

2. Apparatus according to claim 1, wherein the measuring probe comprises a replaceable tip that includes sound canals for the at least one signal generator and the signal receiver.

3. Apparatus according to claim 1, further comprising a pump unit connected via a tube to the measuring probe to control air pressure in the measuring probe, the measuring probe comprising a probe housing, a probe tip a canal arranged for pressure communication between the pump unit and a portion of the person's ear canal which is blocked by the measuring probe when the measuring probe is inserted in the person's ear.

4. Apparatus according to claim 3, wherein the pump unit is contained in a part of the housing which is configured as a handgrip.

5. Apparatus according to claim 4, wherein the handgrip further contains the power supply unit, and the power supply unit includes at least one battery.

6. Apparatus according to claim 3, wherein the pump unit comprises a mechanical, hand-driven pump.

7. Apparatus according to claim 3, wherein the probe tip is arranged for mounting a soft, deformable seal for sealing against the person's ear canal.

8. Apparatus according to claim 3, wherein the housing comprises an elongated part arranged to house the electronic circuit, with the measuring probe mounted at a first end and the display provided on an end of the elongated part opposite the first end, and the housing comprises a handgrip-part containing the power supply unit and the pump unit, the handgrip-part extending from the elongated part.

9. Apparatus according to claim 1, further comprising communication means connectable to other apparatus for transferring data and information to and from the electronic circuit.

10. An apparatus for measuring an oto-acoustic emission from a patient's inner ear, comprising:

a measuring probe including an acoustic generator and an acoustic detector, introduceable into the patient's ear;

an electronic circuit to generate oto-acoustic stimulus signals transmitted by the acoustic generator and for measuring and processing oto-acoustic emission signals received by the acoustic detector;

a housing to hold the measuring probe and the electronic circuit, the housing adapted for being held in a user's hand;

a display mounted on the housing to display data processed by the electronic circuit; and a power supply mounted in the housing.

* * * * *